United States Patent [19]

Vorbrüggen et al.

[11] Patent Number: 5,750,676
[45] Date of Patent: May 12, 1998

[54] PROCESS FOR PREPARING NUCLEOSIDES WITH UNPROTECTED SUGARS

[75] Inventors: Helmut Vorbrüggen; Konrad Krolikiewicz; Bärbel Bennua-Skalmowski, all of Berlin, Germany

[73] Assignee: Hoechst Aktiengesellschaft, Frankfurt am Main, Germany

[21] Appl. No.: 817,802

[22] PCT Filed: Apr. 3, 1996

[86] PCT No.: PCT/EP96/01472

§ 371 Date: Apr. 4, 1997

§ 102(e) Date: Apr. 4, 1997

[87] PCT Pub. No.: WO96/31520

PCT Pub. Date: Oct. 10, 1996

[30] Foreign Application Priority Data

Apr. 3, 1995 [DE] Germany .................. 195 13 330.7

[51] Int. Cl.$^6$ .................. C07H 1/00; C07H 1/06; C07H 19/067; C07H 19/167

[52] U.S. Cl. .................. 536/55.3; 536/26.71

[58] Field of Search .................. 536/55.3, 26.71

[56] References Cited

FOREIGN PATENT DOCUMENTS

| 1313411 | 4/1973 | United Kingdom . |
| 1542442 | 2/1976 | United Kingdom . |

OTHER PUBLICATIONS

Bennua–Skalmowski et al. Tetrahedron Letters vol. 36, No. 43, pp. 7845–7848, 1995.

Derwent Abstract No. 78–77591A, JP53108986 A 780922.

*Primary Examiner*—Gary L. Kunz
*Attorney, Agent, or Firm*—Foley & Lardner

[57] ABSTRACT

A novel process for nucleoside synthesis, which process comprises reacting the free sugar with heterocyclic bases in the presence of silylating agents in an inert solvent containing a Lewis acid.

11 Claims, No Drawings

PROCESS FOR PREPARING NUCLEOSIDES WITH UNPROTECTED SUGARS

The invention relates to a novel process for preparing nucleosides.

German Patent DBP 1919307 describes a process for preparing nucleosides, in which process O-acylated 1-O-acyl, 1-O-alkyl and 1-halo sugars are converted into the corresponding O-acylated nucleosides using silylated heterocyclic bases, such as uracil or 6-azauracil, in the presence of Friedel-Crafts catalysts such as $SnCl_4$.

This process, involving the separate, prior silylation of the heterocyclic bases and their subsequent condensation with the abovementioned O-acylated 1-O-alkyl or 1-O-acyl sugars can, according to DOS 25 08 312, be simplified by carrying out the silylation of the heterocyclic bases and their condensation with O-acylated 1-O-alkyl or 1-O-acyl sugars in one step.

However, all these previous processes, which have been used widely in practice, employ O-acylated sugar derivatives which, like the very frequently used 1-O-acetyl-2,3,5-tri-O-benzoyl-β-D-ribofuranose, have to be prepared from D-ribose by a multistep synthesis.

It has now been found, surprisingly, that this multistep and elaborate conversion of the free sugars, such as D-ribose, into the corresponding O-acylated 1-O-alkyl or 1-O-acyl sugars, such as the already mentioned 1-O-acetyl-2,3,5-tri-O-benzoyl-β-D-ribofuranose, no longer applies, or becomes superfluous, if the free sugars, such as D-ribose or D-glucose, are persilylated, in the presence of the free bases, such as uracil, 6-azauracil, $N^6$-benzoyladenine or $N^2$-acetylguanine, in an inert solvent, with silylating agents, such as hexamethyldisilazane (HMDS) and trimethylchlorosilane (TCS), and a Lewis acid, such as trimethylsilyl triflate, trifluoromethanesulfonic acid, trimethylsilyl nonaflate, perfluorobutanesulfonic acid or $SnCl_4$, is added either simultaneously or subsequently, resulting in the corresponding persilylated nucleosides being produced. These persilylated nucleosides can be converted into the desired free nucleosides by means of transsilylation using boiling methanol.

The invention consequently relates to a novel process for nucleoside synthesis, which process comprises reacting the free sugar with heterocyclic bases in the presence of silylating agents in an inert solvent containing a Lewis acid.

Following neutralization of the Lewis acid, the persilylated nucleosides which have been obtained are converted into the corresponding free nucleosides by means of transsilylation using excess methanol.

When the free sugars and the heterocyclic bases are persilylated with equivalent quantities of hexamethyldisilazane (HMDS) and trimethylchlorosilane (TCS) in boiling absolute acetonitrile, the ammonium chloride which forms sublimes in the reflux condenser and in this way is removed from the reaction mixture.

However, it is often expedient to silylate the mixture of sugar and heterocyclic base only with the calculated quantity of HMDS in the presence of catalytic quantities of TCS, with only ammonia being produced and escaping during heating in acetonitrile. When the reaction is conducted in this manner, the reaction mixture is not contaminated with $NH_4Cl$, and the Lewis acid can be added after the silylation is completed, with a clear solution being formed.

However, any other silylating agent, such as N,O-bis (trimethylsilyl)-acetamide or N,O-bis(trimethylsilyl) acetamide, can be used instead of HDMS/TCS.

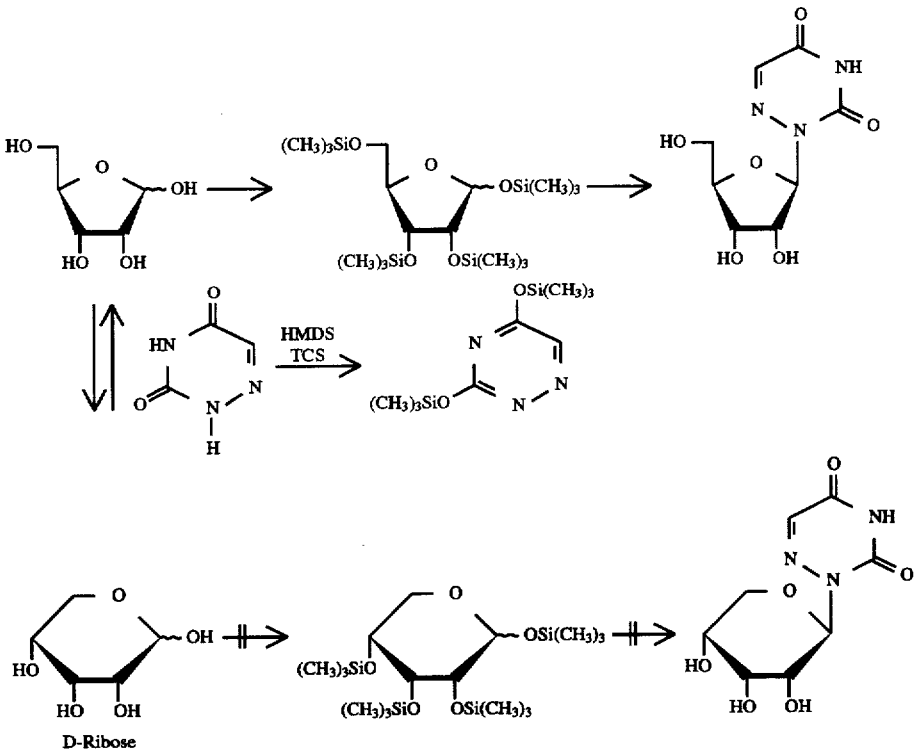

Suitable free sugars are the sugars, such as D-ribose, D-xylose, D-glucose and D-galactose, inter alia, which are customarily used for nucleoside synthesis.

When free D-ribose reacts, the primary 5-hydroxyl group of the furanose form is first of all silylated selectively so that the persilylation results in virtually only persilylated D-ribofuranose, which, together with silylated heterocyclic bases, only gives rise to the corresponding natural D-ribofuranosyl nucleosides.

In individual cases, it can be advantageous, prior to the actual nucleoside synthesis, to selectively react the free primary hydroxyl groups of the sugars, such as the 5-hydroxyl group of D-ribose, with, for example, tert-butyldiphenylsilyl chloride, tert-butyldimethylsilyl chloride, thexyldimethylsilyl chloride or trityl chloride and then subsequently to persilylate these partially protected sugar derivatives with HMDS/TCS in the presence of the heterocyclic bases and convert them with Lewis acids into the corresponding persilylated nucleosides.

Uracil, 6-azauracil, cytosine, $N^4$-acetylcytosine, thymine, 2-thiouracil, 6-aza-2-thiouracil, $N^6$-benzoyladenine, $N^2$-acetylguanine or isobutyrylguanine, and also other deazapurines or azapurines, are preferred as heterocyclic bases.

Acetonitrile, nitromethane, 1,2-dichloroethane, $CS_2$, chloroform, methylene chloride, tetrachloroethylene and toluene, in which solvents a homogeneous solution is usually produced when the mixture of free sugar and free heterocyclic base is persilylated, are used, in particular, as non-polar absolute solvents.

The previously mentioned Lewis acids, and also all the other Lewis acids which are known to be Friedel-Crafts catalysts, such as $SnCl_4$, $SnCl_2$, $TiCl_4$, $BF_3$-$OEt_2$, $FeCl_3$, etc., are suitable for use as Lewis acids and lead to the formation of persilylated nucleosides.

During the working-up, further excess hexamethyldisilazane (HMDS) is added, as a base for neutralizing the Lewis acid, before the reaction mixture in acetonitrile (or another inert solvent) is evaporated. The remaining residue is then boiled, for the transsilylation, for approximately 1—3 h in excess methanol in the presence of fluoride ions (KF or tert-butylammonium fluoride hydrate), after which the mixture is evaporated.

The resulting free uridines are then filtered through a column of strongly basic exchangers such as Dowex 1 (OH form). When the column is eluted with dilute or concentrated ammonia, the neutral sugars which were produced during the nucleoside synthesis are eluted while the acidic uridines are only washed out of the column using 5% formic acid.

If they still do not crystallize, the crude uridines which have been obtained in this way are acetylated, for example with acetic anhydride/pyridine, and, after codistillation with xylene, filtered through a column of silica gel in a toluene/ethyl acetate system. After that, the acetates crystallize and, after recrystallization from methanol or ethanol, can be converted back into the pure, free nucleosides by treatment with methanolic ammonia.

The cytidines, adenosines and guanosines which are synthesized in an analogous manner are loaded onto a column of strongly acidic ion exchangers, such as Dowex 50 or IR-120 (H form), and eluted with increasing concentrations of ammonia after the oligosaccharides have been washed out. In the case of the guanosines, the ion exchanger has subsequently to be washed with dil. HCl.

If they do not crystallize, these prepurified cytidines, adenosines or guanosines are also acetylated with acetic anhydride/pyridine, with the acetates then being purified through a column of silica gel and the crystallized acetates being converted back into the free, pure nucleosides using methanolic ammonia.

In some cases, it is appropriate to dispense with the ion exchanger separation and to purify the crude product, after the transsilylation, directly by acetylation, chromatography on a silica gel column, recrystallization and, finally, hydrolysis with methanolic ammonia.

It is furthermore possible, particularly in the case of the adenosine syntheses, to treat the reducing oligosaccharides, which are produced as by-products, with hydrazine or hydrazine hydrate or semicarbazide in order to convert them into polar derivatives which can easily be separated off.

The following examples are intended to clarify the novel process.

EXAMPLE 1

5 mmol (0.56 g) of azauracil, 10 mmol (1.80 g) of D-glucose, 15 mmol (3.15 ml) of HMDS, 15 mmol (1.89 ml) of trimethylchlorosilane and 25 ml of acetonitrile are mixed and boiled at reflux for 5 hours. A further 5 mmol=1.05 ml of HMDS and 5 mmol (0.63 ml) of TCS are then added and the mixture is once again boiled for 5 hours. The condenser is changed and 7.5 mmol (1.12 g, 0.66 ml) of trifluoromethanesulfonic acid are added and the mixture is boiled at reflux for 3 hours. 5 mmol of HMDS are added and the mixture is concentrated; the residue is taken up in $CH_2Cl_2$ and this solution is extracted by shaking with ice/$NaHCO_3$, after which the organic phase is dried, filtered and concentrated. The residue, weighing 5.78 g, is taken up in MeOH and this solution is boiled at reflux and then concentrated; the residue (2.63 g) in $H_2O$ is loaded onto an exchanger column containing 50 ml of Dowex 1 (OH form) 50–100 mesh. Elution with 2500 ml of 10% $NH_3$ and 3000 ml of water yields 0.85 g of oligosaccharides, while elution with 750 ml of 5% formic acid yields 1.42 g of crude nucleoside. The latter is heated at 80° C. for 1 hour with 50 ml of pyridine and 25 ml of acetic anhydride. This mixture is subsequently concentrated and the residue evaporated 2= with xylene and then dissolved in 100 ml of $CH_2Cl_2$; this solution is extracted by shaking with 50 ml of saturated $NaHCO_3$/ice,→ emulsion, which is filtered through celite followed by washing with $CH_2Cl_2$+$H_2O$. The phases are separated and the aqueous phase is back-extracted 3× with 50 ml of $CH_2Cl_2$ in each case. The $CH_2Cl_2$ phases are dried over $Na_2SO_4$, filtered and concentrated. The crude product, of 1.65 g, is chromatographed through 200 g of silica gel (230–400 mesh) using toluene/ethyl acetate 1:1. After a 1000 ml forerun, 0.64 g, approx. 30%, of 2-(2,3,4,6-tetra-O-acetyl-β-D-glucopyranosyl)-2,3,4,5-tetrahydro-1,2,4-triazine-3,5-dione is eluted in the following 1000 ml. Recrystallization from methanol results in pure tetraacetate having a melting point of 208°–210° C.

EXAMPLE 2

5 mmol (0.56 g) of azauracil, 5 mmol (0.75 g) of D-ribose, 14 mmol (2.92 ml) of HMDS, 14 mmol (1.77 ml) of trimethylchlorosilane and 50 ml of acetonitrile are mixed and boiled at reflux for 1½ hours. The mixture is subsequently cooled down to +10°, after which 7.5 mmol (0.66 ml) of trifluoromethanesulfonic acid are added and the mixture is boiled at reflux for 8 hours. After having been cooled down to 24°, it is concentrated on a rotary evaporator and the residue is boiled for 30 minutes with 50 ml of methanol. This mixture is concentrated in vacuo and the residue is then stirred at 60° for 2 hours with 20 ml of pyridine and 10 ml of acetic anhydride.

The mixture is subsequently concentrated and the residue is distilled 2× with 20 ml of xylene on each occasion. The residue is chromatographed on 100 g of silica gel (230–400 mesh) using toluene/ethyl acetate 1:1, yielding 0.9 g of crude azauridine triacetate.

Recrystallization from ethyl acetate/hexane yielded 0.62 g (=33.4%) of pure azauridine triacetate having a melting point of 102°–103°.

EXAMPLE 3

A mixture of 15 mmol (2.25 g) of dry D-ribose and 5 mmol (0.565 g) of 6-azauracil is silylated for 2 hours with 15 ml of HMDS and 0.1 ml of trimethylchlorosilane in 30 ml of boiling absolute acetonitrile. After concentrating by evaporation in vacuo, the residue is kept at 80°/1 mm for 2 hours and then dissolved in 40 ml of boiling absolute acetonitrile; 5.5 mmol (0.99 ml) of trimethylsilyl triflate in 10 ml of acetonitrile are then added at 80° C. and within the space of 45 minutes. After the mixture had been kept at 80° C. for 7 hours, 20 ml of a saturated, aqueous solution of $NaHCO_3$ are added at 24° C. and the resulting dark-colored mixture is stirred at 24° C. for 4 hours. Following concentration, the dark-colored residue is extracted with 3×100 ml of boiling methanol and the extracts are concentrated. The residue is dissolved in approx. 10 ml of water and absorbed to approx. 20 g of $SiO_2$, which is loaded onto a column of 200 g of $SiO_2$ (previously treated for 4 hours with 25% $NH_3$ (9:1) until a clear filtrate is obtained). Elution with ethanol/25% $NH_3$ (9:1) first leads to 675 ml of eluate containing quantities of sugar and also traces of 6-azauracil. The following 650 ml yield 0.84 g (68.3%) of slightly colored crude 6-azauridine. The latter is treated in water with active charcoal and then crystallized from ethanol, yielding pure crystalline 6-azauridine (melting point 159°–161° C.).

We claim:

1. A process for preparing nucleosides, which comprises reacting free sugars with hetero-cyclic bases in the presence of at least one silylating agent in an inert solvent containing a Lewis acid.

2. The process as claimed in claim 1, wherein the at least one silylating agent is selected from the group consisting of hexamethyldisilazane, trimethylchlorosilane, N,O-bis) trimethylsilyl) acetamide and N,O-bis(trimethylsilyl) acetamide.

3. process as claimed in claim 1, wherein one silylating agent is used.

4. A process as claimed in claim 1, wherein at least two different silylating agents are used.

5. A process as claimed in claim 1, wherein hexamethyldisilazane and trimethylchlorosilane are used as silylating agents.

6. A process as claimed in claim 1, wherein the Lewis acid is selected from the group consisting of trimethylsilyl triflate, trifluoromethanesulfonic acid, trimethylsilyl nonaflate, perfluorobutane sulfonic acid and Friedel-Crafts catalysts.

7. A process as claimed in claim 6, wherein the Friedel-Crafts catalyst is selected from the group consisting of $SnCl_4$, $SnCl_2$, $TiCl_4$, $BF_3$-$OEt_2$ and $FeCl_3$.

8. A process as claimed in claim 1, wherein the inert solvent is selected from the group consisting of acetonitrile, nitromethane, 1,2-dichloroethane, $CS_2$, chloroform, methylene chloride, tetrachloroethylene, and toluene.

9. A process as claimed in claim 1, wherein the reaction mixture is heated.

10. A process as claimed in claim 1, wherein the sugar is selected from the group consisting of D-ribose, D-xylose, D-glucose, and D-galactose.

11. A process as claimed in claim 1, wherein the heterocyclic base is selected from the group consisting of uracil, 6-azauracil, cytosine, $N^4$-acetylcytosine, thymine, 2-thiouracil, 6aza-2-thiouracil, $N^6$-benzoyladenine, $N^2$-acetylguanine and isobutyrylguanine.

* * * * *

UNITED STATES PATENT AND TRADEMARK OFFICE
CERTIFICATE OF CORRECTION

PATENT NO. : 5,750,676
DATED : May 12, 1998
INVENTOR(S) : VORBRÜGGEN et al.

It is certified that error appears in the above-identified patent and that said Letters Patent is hereby corrected as shown below:

Column 6, Claim 2, line 5, please delete

"acetamide" and insert --trifluoroacetamide--.

Signed and Sealed this

First Day of December, 1998

BRUCE LEHMAN

*Attest:*

*Attesting Officer*  Commissioner of Patents and Trademarks

UNITED STATES PATENT AND TRADEMARK OFFICE
CERTIFICATE OF CORRECTION

PATENT NO. : 5,750,676
DATED : May 12, 1998
INVENTOR(S) : VORBRÜGGEN et al.

It is certified that error appears in the above-identified patent and that said Letters Patent is hereby corrected as shown below:

At Column 6, Claim 2, line 3, following "N,O-bis", please delete ")" and insert -- ( --.

Signed and Sealed this

Fifth Day of January, 1999

Attest:

Attesting Officer

Acting Commissioner of Patents and Trademarks